(12) United States Patent
Barton et al.

(10) Patent No.: US 7,033,100 B2
(45) Date of Patent: Apr. 25, 2006

(54) GLOVE WITH INTEGRATED ANTISEPTIC ABSORBER

(76) Inventors: Brad Barton, 14915 SW. 100th, Tigard, OR (US) 97224; Richard Barton, 14915 SW. 100th, Tigard, OR (US) 97224

( * ) Notice: Subject to any disclaimer, the term of this patent is extended or adjusted under 35 U.S.C. 154(b) by 116 days.

(21) Appl. No.: 10/719,908

(22) Filed: Nov. 21, 2003

(65) Prior Publication Data
US 2005/0111898 A1    May 26, 2005

(51) Int. Cl.
*A46B 5/04*    (2006.01)
*B43K 5/14*    (2006.01)
(52) U.S. Cl. .......................... 401/7; 401/132
(58) Field of Classification Search .............. 401/7, 401/132–135; 604/1–3
See application file for complete search history.

(56) References Cited

U.S. PATENT DOCUMENTS

| | | | |
|---|---|---|---|
| 1,161,719 A * | 11/1915 | Norton | ........................ 601/154 |
| 2,265,329 A | 12/1941 | Wachs | |
| 2,790,982 A * | 5/1957 | Schneider | ...................... 401/7 |
| 3,342,182 A | 9/1967 | Charos | |
| 3,596,798 A | 8/1971 | Smith | |
| 3,608,708 A | 9/1971 | Storandt | |
| 4,034,853 A | 7/1977 | Smith | |
| 4,122,554 A | 10/1978 | Stager | |
| 4,185,330 A | 1/1980 | Stager | |
| 4,186,445 A | 2/1980 | Stager | |
| 4,645,251 A | 2/1987 | Jacobs | |
| 4,677,697 A | 7/1987 | Hayes | |
| 4,768,818 A | 9/1988 | Kolic | |
| 4,788,733 A | 12/1988 | Lerner | |
| 4,845,781 A | 7/1989 | Strickland et al. | |
| 4,902,283 A | 2/1990 | Rojko et al. | |
| 4,928,322 A | 5/1990 | Bradfield | |
| 4,937,881 A | 7/1990 | Heise | |
| 4,959,881 A | 10/1990 | Murray | |
| 4,980,943 A | 1/1991 | Barber | |
| 5,003,638 A | 4/1991 | Miyake et al. | |
| 5,020,159 A | 6/1991 | Hellickson | |
| 5,089,205 A | 2/1992 | Huang et al. | |
| 5,169,251 A * | 12/1992 | Davis | ........................... 401/7 |
| 5,186,322 A | 2/1993 | Harreld et al. | |
| 5,301,806 A | 4/1994 | Olson | |
| 5,335,373 A | 8/1994 | Dresdner et al. | |
| 5,357,636 A | 10/1994 | Dresdner, Jr. et al. | |
| 5,438,708 A | 8/1995 | Jacovitz | |
| 5,679,399 A | 10/1997 | Shlenker et al. | |
| 5,704,670 A | 1/1998 | Surplus | |
| 5,767,163 A | 6/1998 | Kundsin | |
| 5,806,668 A | 9/1998 | Bixby | |
| 5,864,883 A | 2/1999 | Reo | |
| 5,956,770 A | 9/1999 | Dennis | |
| 5,961,167 A | 10/1999 | Gilley | |
| 5,965,276 A | 10/1999 | Shlenker et al. | |
| 5,987,645 A | 11/1999 | Teaster | |
| 6,024,970 A * | 2/2000 | Woodard | .................... 424/402 |
| 6,116,668 A | 9/2000 | Carpol | |

(Continued)

FOREIGN PATENT DOCUMENTS

DE         10040210         9/2001

(Continued)

Primary Examiner—David J. Walczak
(74) Attorney, Agent, or Firm—Chernoff Vilhauer McClung & Stenzel, LLP

(57) ABSTRACT

A glove is usable for removing fluid material from surfaces and, in a particular embodiment, is usable for cleaning blood or other bio-hazardous material from surfaces.

13 Claims, 2 Drawing Sheets

U.S. PATENT DOCUMENTS

| | | |
|---|---|---|
| 6,168,019 B1 | 1/2001 | Olson |
| 6,170,426 B1 * | 1/2001 | Thorsbakken ................ 118/43 |
| D446,368 S | 8/2001 | Pizarro |
| 6,385,806 B1 | 5/2002 | Katakura et al. |
| 6,393,614 B1 | 5/2002 | Eichelbaum |
| 6,398,443 B1 | 6/2002 | Barela |
| 6,423,328 B1 | 7/2002 | Chou |
| 6,481,766 B1 | 11/2002 | May et al. |
| 6,511,111 B1 | 1/2003 | Dooley |
| 6,513,998 B1 | 2/2003 | Barry |
| 6,669,387 B1 * | 12/2003 | Gruenbacher et al. ......... 401/7 |
| 2002/0055312 A1 | 5/2002 | Beraznik |
| 2002/0116746 A1 | 8/2002 | Williams |
| 2002/0177828 A1 | 11/2002 | Batich et al. |
| 2002/0178482 A1 | 12/2002 | Samuelsson et al. |

FOREIGN PATENT DOCUMENTS

| | | |
|---|---|---|
| FR | 2 694 877 | 2/1994 |
| FR | 2 702 947 | 9/1994 |
| FR | 2 813 777 | 3/2002 |
| GB | 2 061 709 | 5/1981 |
| GB | 2 113 977 | 8/1983 |
| GB | 2 231 027 | 11/1990 |
| JP | 6136603 | 5/1994 |
| JP | 7213474 | 8/1995 |
| JP | 8206049 | 8/1996 |
| JP | 11012820 | 1/1999 |
| JP | 2001187011 | 7/2001 |
| WO | WO 96 10356 | 4/1996 |
| WO | WO 03 030701 | 4/2003 |

* cited by examiner

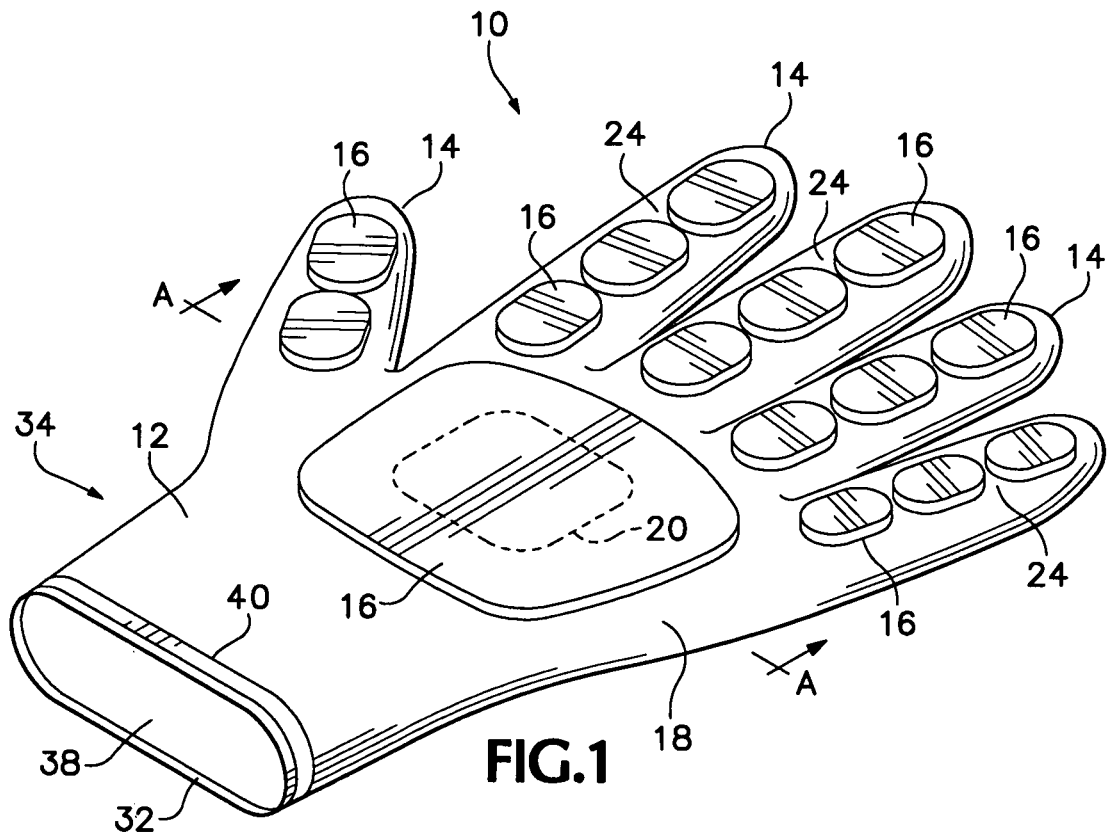
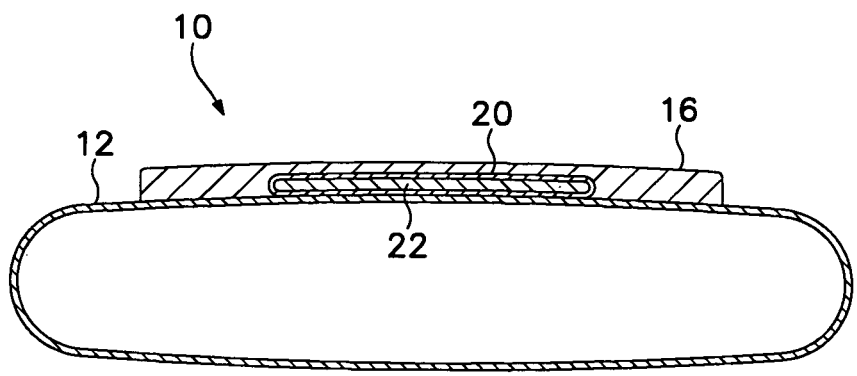

GLOVE WITH INTEGRATED ANTISEPTIC ABSORBER

BACKGROUND OF THE INVENTION

The present invention relates to a glove used for removing fluid material from surfaces, and in one particular aspect, to a glove used for cleaning blood or other bio-hazardous material from surfaces.

In recent years, there has been growing concern regarding the spread of communicable illnesses through casual contact with bio-hazardous materials including blood and other biological fluids. For that reason, any surface upon which exposed blood or other biological fluid is spilled should be promptly cleaned and disinfected to minimize the potential for inadvertent communication of illnesses. Such spills may occur anywhere, but are particularly recurrent in areas such as hospitals, athletic arenas such as gymnasiums, boxing rings, and basketball courts as well as workplace areas such as construction sites and manufacturing plants.

Unfortunately, the communication of illnesses may potentially occur during even the brief contact with blood or other biological fluids during the time a person is cleaning them from surfaces. For that reason, the Occupational Safety and Health Administration (OSHA) has promulgated detailed regulations pertaining to the manner in which blood or other bio-hazardous materials are to be safely removed from surfaces. These procedures include the requirements that persons cleaning such surfaces wear fluid-impermeable gloves and that any cleaning materials such as sponges or other absorbent material be disposed of in containers clearly marked as containing bio-hazardous material. In addition, many institutions not bound by these OSHA regulations either voluntarily comply with them, or adopt similar procedures.

To facilitate the procedure of cleaning blood or other bio-hazardous material from a surface, pre-packaged "kits" are available that contain a number of items necessary to safely clean and disinfect a surface from such material. One such kit, for example, includes one or more latex gloves, a packaged congealing agent, a plastic scoop, packaged disinfectant wipes, one or more paper towels, and a plastic bio-hazard bag labeled with the international symbol for bio-hazardous waste. When using such a kit on a blood spill on a basketball court, for example, a person may first sprinkle the congealing agent over the spill which causes the blood to coagulate into a more solid form. Then, wearing gloves, the person may scoop the coagulated blood into the plastic bio-hazard bag. Because the surface will still likely contain blood or blood-borne bacteria, the person may then scrub the spill area with the disinfectant wipes and then dry the area with the paper towels, being sure to place the plastic scoop, the wipes, and the paper towels inside the bio-hazard bag for safe disposal.

One drawback of such kits are that they are bulky and do not facilitate the quick removal of fluids from a surface due to the multiple steps involved in coagulating the blood or other biological fluid, disinfecting and drying the contaminated surface, and then disposing of all the materials in a biohazard bag. Further, the risk of accidental contact with the hazardous material increases proportionally with each additional step in the disposal process, as the latex glove may be punctured, the fluid may splatter beyond the boundaries of the latex glove, etc.

Another type of existing product that facilitates the removal of bio-hazardous material from a surface is an absorbent bag or glove as exemplified by U.S. Pat. No. 6,481,766 B1 and U.S. Pat. No. 5,806,668. Each of these products is designed to enclose a person's hand and often shaped like a glove or a mitten. Absorbent material is affixed to the palm-side surface of these products so that a person may clean fluid material from a contaminated surface. The absorbent material is typically impregnated with an antiseptic to both neutralize any bacteria or virus present in the fluid and disinfect the surface. Impregnating the absorbent material with an antiseptic, however, is problematical. Absorbent material impregnated with a dry or powdered antiseptic is relatively ineffective, particularly with respect to the absorption and disposal of viscous fluids because while the powdered antiseptic may neutralize most of the fluid absorbed, the surface is inadequately disinfected because the absorbent material is not sufficiently wetted. Conversely, if the absorbent material is impregnated with fluid antiseptic, the absorbent material must be vacuum sealed during storage to prevent the antiseptic from evaporating.

What is desired, then, is an improved system for the safe removal of bio-hazardous material from surfaces.

BRIEF DESCRIPTION OF THE DRAWINGS

FIG. 1 is a perspective view of a glove that incorporates the disclosed system where the glove is shaped to receive a person's hand.

FIG. 2 is a cross sectional view taken along line A—A in FIG. 1.

DETAILED DESCRIPTION

Figure 3:
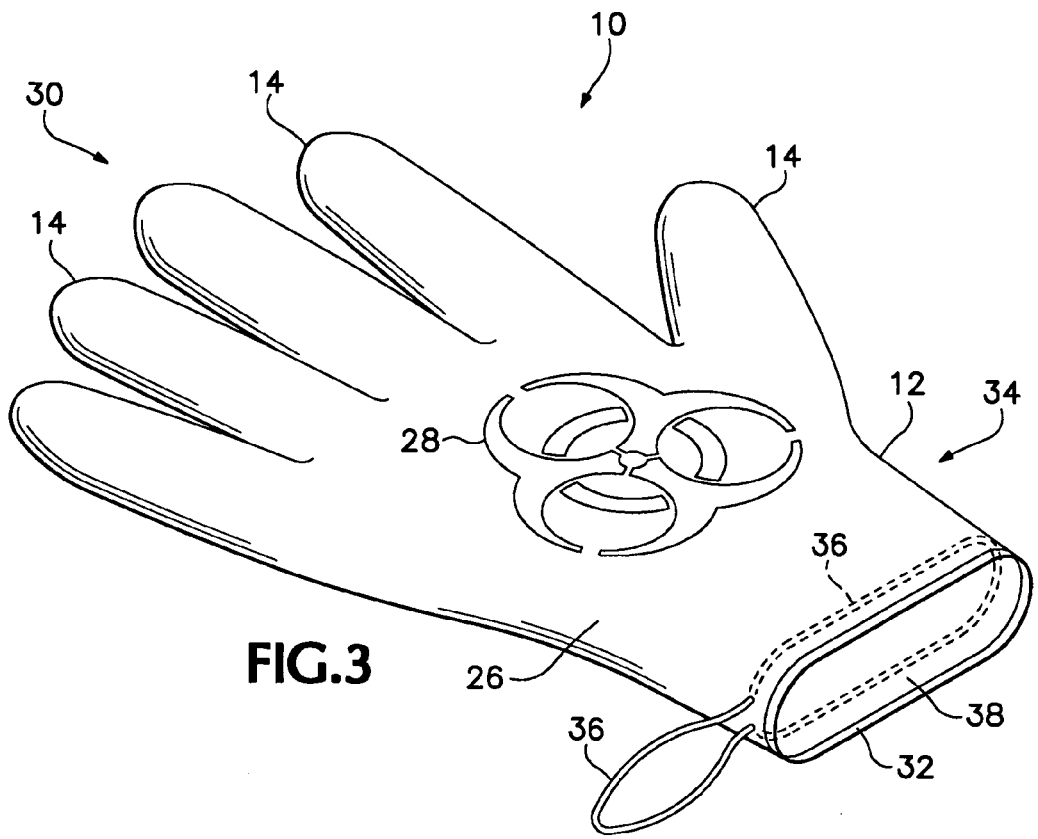
FIG. 3 is a perspective view of the glove of FIG. 1 after being everted.

Referring to FIGS. 1 and 2, a cleaning member 10 may comprise a fluid-impermeable liner 12 having a shape suitable to enclose at least a portion of a person's hand. The fluid-impermeable liner 12 may comprise any appropriate material such as latex, rubber, vinyl, plastic, etc. The liner 12 may optionally define a plurality of finger portions 14 each shaped to enclose a finger on a person's hand so that the cleaning member 10 takes the form of a glove. Alternatively, the glove 10 may be of a form that omits the finger portions 14 so that the cleaning member 10 may take the form of a mitten. For convenience, the cleaning member 10 will hereinafter be referred to as a "glove" 10, though it should be understood that the glove 10 may be of any arbitrary shape that at least partially encloses a human hand. Preferably, the glove 10 is shaped to completely enclose a human hand to at least the wrist.

The glove 10 may also include fluid-absorbing material 16 affixed to a palm-side outer surface 18 of the liner 12 of the glove 10. The fluid-absorbing material 16 may be affixed to the liner 12 in any convenient manner, e.g. through the use of an adhesive, or other desired means. The glove 10 may also preferably include a fluid-impermeable member 20 positioned adjacent the fluid-absorbing material 16. The fluid-impermeable member 20 preferably contains antiseptic fluid 22 and isolates the fluid 22 from the fluid-absorbing material 16 until the impermeable member 20 is intentionally ruptured.

When fluid material, such as blood for example, is desired to be removed from a contaminated surface, a person may insert his or her hand into the glove 10 and rupture the fluid-impermeable member 20 by squeezing the glove into a fist or by any other appropriate means. Once the fluid-impermeable member 20 is ruptured, the antiseptic material is absorbed into the adjacent fluid-absorbing material 16 at which point the glove 10 may be used to clean and disinfect the contaminated surface. The glove 10 simplifies the process by which bio-hazardous material is cleaned from a surface by integrating the glove-shaped liner 12 with both an antiseptic 22 and fluid-absorbing material 16, obviating the need for antiseptic wipes, and also if desired integrating the liner 12 with coagulating agents. Further, it should be appreciated that the glove 10, unlike the aforementioned prior art, does not need to be vacuum-enclosed to prevent the fluid antiseptic 22 from evaporating.

The fluid-absorbing material 16 is preferably affixed over a majority of the portion of the liner 12 corresponding to the palm of a hand inserted into the glove 10. To increase the capacity of the glove 10 to absorb additional quantities of fluid, it may be desirable to affix fluid absorbing material 16 to the outer surface of the finger portions 14 of the liner 12 as well as the palm-side outer surface 18, as shown in FIG. 1. If this option is utilized, those portions of the fluid absorbing material 16 affixed to the finger portions 14 may include gaps 24 corresponding to the joints of the fingers inserted into the glove 10 to facilitate the manual dexterity of the user and to more easily permit the glove 10 to be squeezed into a fist when selectively rupturing the fluid-impermeable member 20. The fluid-absorbing capacity of the glove 10 may be increased even further if the glove 10 is shaped like a mitten so that the fluid-absorbing material 16 may continuously extend over that portion of the outer surface of the liner 12 that corresponds to the inner portion of the hand of a person using the glove 10.

The fluid-impermeable member 20 may be composed of any material capable of rupturing under manually applied pressure, such as gelatin, plastic, etc. Such materials are well known in industry. One appropriate material, for example, is a gelatin composition used to form imitation blood capsules that may be selectively ruptured when performing visual effects. Another appropriate material might be a plastic composition similar to those used to contain controlled amounts of ketchup, mustard, and other condiments dispensed to take-out customers of fast-food restaurants.

The fluid-impermeable member 20 may be configured in any appropriate and desired shape. For example, the fluid-impermeable member 20 may be of a generally cylindrical shape, such as a capsule. Alternatively, the fluid-impermeable member 20 may be of a generally planar shape that extends over a large portion of the palm-side outer surface 18 of the glove 10 so that the antiseptic fluid is more widely dispersed throughout the fluid-absorbing material 16 after being ruptured.

FIGS. 1 and 2 show the fluid-impermeable member 20 positioned between the fluid-absorbing material 16 and the fluid-impermeable liner 12. This configuration facilitates retention and absorption of the antiseptic fluid 22 throughout the fluid absorbing material 16 once ruptured. Alternatively, however, the fluid-impermeable member 20 may be positioned adjacent the outer surface of the fluid-absorbing material 16, if desired.

The fluid-impermeable member 20 may be designed to rupture using any desired action or combinations of actions. Preferably, the fluid-impermeable member 20 is capable of rupturing under hand pressure that results from any one of a number of chosen manual actions, such as squeezing a hand inserted into the glove 10 into a fist, putting pressure on the fluid impermeable member 20 with a finger of the hand not enclosed by the glove 10, by pressing the palm-side outer surface 18 against a rigid surface such as a table or floor, or any other desired method.

The antiseptic fluid 22 may comprise any desired and appropriate composition having antiseptic properties. For example, the antiseptic fluid may comprise an iodine solution, or a mixture of ethyl alcohol and chloroxylenol, or any selective one of a number of known antiseptic fluids. Preferably, the chosen antiseptic is capable of neutralizing known blood-borne bacteria. Optionally, the antiseptic fluid 22 may include a coagulating agent to prevent spillage.

In an alternate embodiment, it may be desirable to impregnate the fluid-absorbing material 16 with a dry antiseptic, such as sodium iodide, potassium iodide, or sodium hypochlorite, for example. In this instance, the fluid-impermeable member 20 may not be necessary, or, if the chosen dry antiseptic is activated after being hydrated, the fluid-impermeable member may simply contain water. In still another embodiment, the fluid-absorbing material 16 may be impregnated with a dry coagulating agent, such as sodium dichloro isocyanurate while the fluid-impermeable member 20 contains a fluid-antiseptic.

Though the glove 10 is primarily intended to be used to clean and disinfect surfaces containing spilled blood or other bio-hazardous materials, the glove 10 may be adapted for use in cleaning and disinfecting surfaces contaminated with more mundane materials, such as household bacteria from food and the like. In that event, the chosen antiseptic need not be capable of neutralizing blood-borne bacteria, and may comprise a simple alcohol solution or other common household disinfectant.

As previously mentioned, OSHA regulations require hospitals and other workplaces to dispose of any material containing bio-hazardous agents, such as blood, in a specially marked biohazard disposal bag. Such bags typically are either colored bright orange or are red and labeled with the international symbol for bio-hazardous waste. To this end, the glove 10 may be included within a cleaning kit that optionally includes such a biohazard bag, and if desired, a packaged congealing agent, a plastic scoop, one or more paper towels, or any combination of the preceding. Alternatively, referring to FIG. 3 which shows the glove 10 in an everted condition, i.e. turned inside out, the glove 10 may include a fluid-impermeable liner 12 having an inner surface 26 marked as a biohazard bag so that once the glove 10 has been used to clean and disinfect a surface, the glove 10 may be everted so that the glove itself becomes a biohazard bag 30 that contains the bio-hazardous material inside it. In this instance, the inner surface 26 should either be either colored bright orange or colored red and include the symbol 28. These examples of the coloration and markings of the biohazard bag are illustrative only, but preferably, the biohazard bag 30 is marked in accordance with the current OSHA regulations. Also, the biohazard markings may be colored or imprinted on the fluid-impermeable liner 12, or may be colored or imprinted on an inner layer affixed to the liner 12.

To facilitate the selective eversion of the glove 10 to create a biohazard bag 30, the glove 10 may include a stiffener 32 positioned about a wrist portion 34 of the glove 10. When it is desired to evert the glove 10, a person need only grasp the wrist portion 34 with his or her free hand at the stiffener 32 and pull the glove off. If the glove 10 has a liner 12 of latex or other similar material, the glove 10 will evert as it is pulled off. If the glove is made or rubber or some other thick material that does not easily evert, it may be necessary to grip the glove with the enclosed hand by curling the inserted fingers or otherwise to cause the glove to evert when pulling the wrist portion 34 with the free hand.

The glove 10 may optionally include a drawstring 36 used to seal the opening 38 at the wrist portion 34 once a person's hand is removed. Alternatively, the opening 38 may be sealed using adhesive material 40 (shown in FIG. 1) on the outer surface of the liner 12 along the wrist portion 34, or include a zip-lock type seal, or other desired sealing mechanism.

Figure 4:
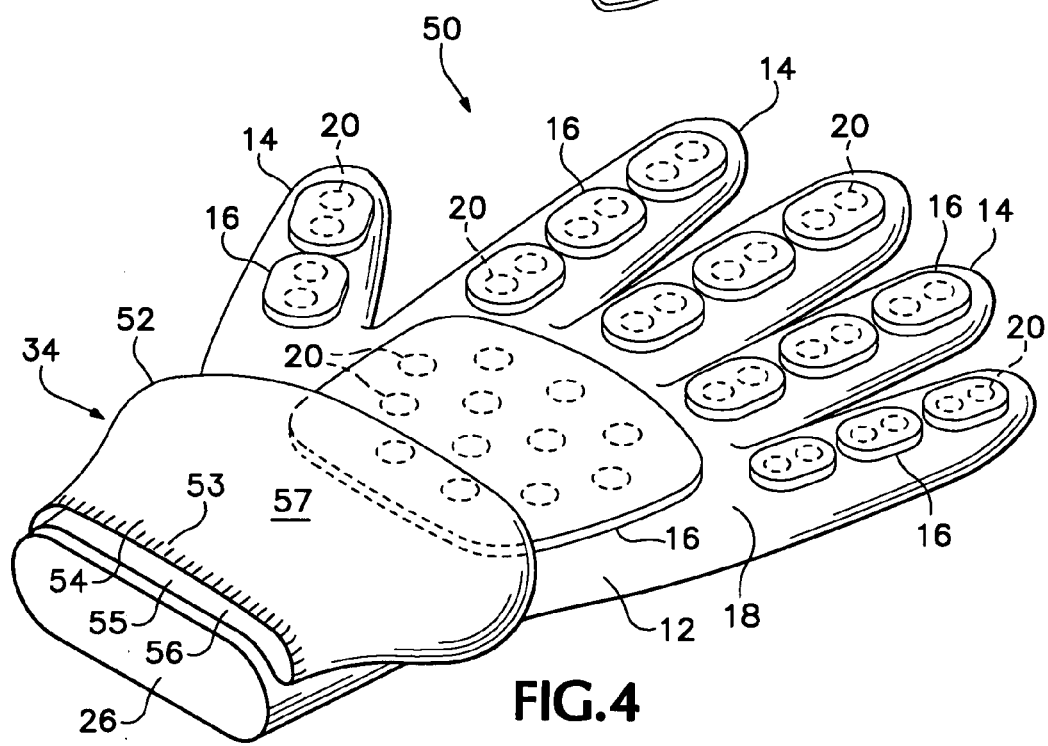
FIG. 4 is a perspective view of a glove that incorporates an alternate embodiment of the disclosed system.

FIG. 4 shows a glove 50, similar to the glove 10 in that the glove 50 includes fluid absorbing material 16 affixed to the fluid impermeable liner 12 and is disposed over the finger portions 14 as well as the portion of the glove 50 corresponding to the palm of an inserted hand. The glove 50, however, includes a plurality of fluid impermeable members 20 dispersed throughout the glove 50 including the finger portions 14, where each fluid-impermeable member is adjacent fluid absorbing material 16. In this manner, the antiseptic fluid 22 is more evenly dispersed through the fluid absorbing material 16 when the fluid impermeable members 20 are selectively ruptured by, for example, clenching an inserted fist, pressing the glove 10 against a surface, etc.

The glove 50 may also include a liner 12 that has an inner surface 26 that functions as a biohazard bag when everted. When the glove 50, the glove 10, or any other similar glove is everted in the manner previously described, i.e. by using the free hand to pull the wrist portion 34 over the finger portions 14, the fluid absorbing material 16 may tend to compress. This may be problematical if the fluid absorbing material has absorbed exceptionally large quantities of fluid containing bio-hazardous or other infectious material, because the compression may tend to release the fluids back onto the surface being cleaned, onto the skin of the person using the glove, or onto some other undesired location.

To counter this problem, the glove 50 may include a containment bag 52 having a surface 54 defining an opening 56 into the bag 52. The containment bag 52 preferably includes an elastic band 53 around the opening 56, or includes some other material capable of stretching so that the opening 56 may have a variable size. The surface 54 may have a first portion 55 that is preferably affixed to the wrist portion 34 of the glove 50 over at least half the circumference of the wrist portion 34, and preferably the half of the wrist portion adjoining the palm-side outer surface 18. Alternatively, the first portion 55 may be affixed to the wrist potion 34 over less than half of the circumference of the wrist portion 34, or may be affixed to another part of the liner 12 instead of the wrist portion 34, or may be affixed to the wrist portion 34 opposite of or offset from the palm-side outer surface 18. The surface 54 may also include a second portion 57 that is not affixed to the liner 12 so that the second portion 57 may be moved, or stretched via the elastic band 53, to a containment position where the containment bag 52 at least partially, and preferably completely, covers the fluid-absorbing material 16.

When it is desired to evert the glove 50, a user may first stretch the opening 56 of the containment bag 52 over the finger portions 14 of the glove 50 and back to the wrist portion 34 so that the containment bag encloses the glove 50 and covers the fluid absorbing material 16. The user may then grasp the wrist portion 34 together with the surface 54 of the containment bag and evert the glove 50 in the manner previously described so that any fluids escaping from the glove 50 due to the compression of the fluid absorbing material 16 is captured within the containment bag 52 during the glove eversion process. Once everted, the glove 50 becomes a bio-hazard container. If the containment bag 52 does not include an elastic band 53 or other material capable of stretching, the bag 52 and the opening 56 may be sufficiently large to pull over and enclose the glove 50 without stretching the surface 54.

Alternatively, if the liner 12 of the glove 50 comprises a sufficiently stiff material, such as rubber, so that it is feasible to remove an inserted hand without everting the glove 50, the containment bag 52 may be appropriately marked as a biohazard bag. In this instance, the containment bag may be pulled or stretched over the glove 50 immediately prior to the removal of a person's hand from the glove 50 and optionally sealed using a drawstring 36, or other appropriate means.

The terms and expressions that have been employed in the foregoing specification are used therein as terms of description and not of limitation, and there is no intention, in the use of such terms and expressions, of excluding equivalents of the features shown and described or portions thereof, it being recognized that the scope of the invention is defined and limited only the claims that follow.

The invention claimed is:

1. An antiseptic cleaning apparatus comprising:
   (a) a fluid-impermeable liner shaped to at least partly enclose a person's hand, said liner having a palm-side outer surface;
   (b) fluid-absorbing material affixed to said palm-side outer surface and impregnated with a coagulant; and
   (c) fluid contained in at least one fluid-impermeable member that isolates said fluid from said fluid-absorbing material, said member located adjacent said fluid-absorbing material and capable of rupturing under manual pressure.

2. The apparatus of claim 1 where said fluid is an antiseptic.

3. The apparatus of claim 1 where said liner is shaped like a glove.

4. The apparatus of claim 1 where said liner includes a plurality of finger portions, with fluid-absorbing material affixed to at least one of said finger portions.

5. The apparatus of claim 4 where said member is positioned adjacent the fluid-absorbing material affixed to at least one of said finger portions.

6. The apparatus of claim 1 where said fluid-absorbing material is also impregnated with a dry antiseptic and said fluid comprises water.

7. An antiseptic cleaning apparatus comprising:
   (a) a fluid-impermeable liner shaped to enclose a person's hand, said liner having a palm-side outer surface and an opening sized to receive a person's hand;
   (b) fluid-absorbing material affixed to said palm-side outer surface and impregnated with a coagulant; and
   (c) fluid antiseptic contained in at least one fluid-impermeable member that isolates said fluid antiseptic from said fluid-absorbing material, said member located adjacent said fluid-absorbing material and capable of rupturing under manual pressure.

8. The apparatus of claim 7 where said member is located between said liner and said fluid-absorbing material.

9. The apparatus of claim 7 where said liner is shaped like a glove.

10. The apparatus of claim 7 where said liner includes a plurality of finger portions, with fluid-absorbing material affixed to at least one of said finger portions.

11. The apparatus of claim 10 where said member is positioned adjacent the fluid-absorbing material affixed to said finger portions.

12. The apparatus of claim 7 where said liner is evertable so as to form a biohazard container for said fluid-absorbing material and said member.

13. The apparatus of claim 7 where said liner includes an opening capable of receiving a person's hand, and a sealing member operable to seal said opening after said liner is everted.

* * * * *